United States Patent [19]
Hubeau

[11] Patent Number: 4,503,011
[45] Date of Patent: Mar. 5, 1985

[54] APPARATUS FOR DETERMINING THE BLOOD GROUP OF AN INDIVIDUAL

[75] Inventor: Jean-Pierre Hubeau, Montigny-Le-Tilleul, Belgium

[73] Assignee: Finamex Finance Corporation, Panama, Panama

[21] Appl. No.: 441,618

[22] Filed: Nov. 15, 1982

[30] Foreign Application Priority Data

Nov. 18, 1981 [CH] Switzerland .......................... 7400/81

[51] Int. Cl.³ ...................... G01N 33/48; G01N 35/02
[52] U.S. Cl. ...................................... 422/73; 365/244; 422/63; 422/102; 436/47; 436/69
[58] Field of Search ...................... 73/864.91; 206/569; 350/535, 536; 356/330, 39, 443, 444, 244, 246; 422/73, 61, 63, 65–67, 58, 102; 435/291, 287; 436/44, 47, 66, 67, 69

[56] References Cited

U.S. PATENT DOCUMENTS

| | | | |
|---|---|---|---|
| 3,005,375 | 10/1961 | Sherman | 356/244 |
| 3,533,744 | 10/1970 | Unger | 422/65 X |
| 3,992,112 | 11/1976 | Arion | 356/39 X |
| 4,190,314 | 2/1980 | Goldsmith | 350/535 |
| 4,224,032 | 9/1980 | Glover et al. | 422/65 X |
| 4,269,803 | 5/1981 | Jessop | 422/58 X |

FOREIGN PATENT DOCUMENTS 0046430 2/1982 European Pat. Off. .............. 356/39

Primary Examiner—Barry S. Richman
Assistant Examiner—Michael S. Gzybowski
Attorney, Agent, or Firm—Walter H. Schneider

[57] ABSTRACT

An apparatus for determining the blood group of an individual. The apparatus comprises a carrier plate slidably mounted for horizontal movement and adapted to support an analysis holder. The analysis holder is provided with several series of cavities adapted to hold blood samples, agglutination reactants, and mixtures of the two for analysis. A block of distribution needles associated with pumping means is slidably mounted for vertical movement. The number of needles in the distribution block and the number cavities in each series in the analysis holder is the same. The movements of the block of distribution needles and of the carrier plate are synchronized, when initiated, so as to cause blood samples and reactants to be pumped from their respective cavities in the analysis holder through their corresponding needles to analysis cavities. Analysis is by optical density detecting means associated with means for displaying the analytical results.

2 Claims, 12 Drawing Figures 4,503,011

APPARATUS FOR DETERMINING THE BLOOD GROUP OF AN INDIVIDUAL

BACKGROUND OF THE INVENTION

1. Field of the Invention

The present invention relates to blood analysis. More particularly, the present invention relates to an apparatus for analyzing blood samples. Still more particularly, the present invention relates to an apparatus for analyzing the blood of an individual to determine blood group and Rheus positive and negative factor.

2. Description of the Prior Art

Devices for determining the blood group of an individual are well known and comprise, in general, a combinations of means for preparing a sample of the blood of the individual, mixing a specific quantity thereof with agglutination reactants, analyzing the mixture for the presence or absence of an agglutination reaction, and visually displaying the results of the analysis. These various devices all suffer from certain disadvantages particularly with respect to the detection or analysis of the agglutinating reaction. None appears to provide a completely satisfactory solution to the critical problem of producing a homogeneous mixture of blood sample and reactant on which the agglutination analysis is made, with the result that the analysis may lead to erroneous or inaccurate results in crtcial situtations.

One such apparatus or device for determining the blood group of an individual is disclosed and described in Swiss patent application Ser. No. 306/81-3. In accordance with the device of this Swiss patent application, a technique is employed for mixing the blood sample with the agglutination reactant which comprises subjecting the blood sample together with a pouch containing the reactant to the crushing action of two rolls rotating in the same direction. Detection of agglutination of the blood sample-reactant mixture is then determined by measuring its optical density. An accurate determination of a quantitative threshold of the optical density of the mixture is difficult, if not impossible, to make because the intensity of agglutination depends upon the mixture analyzed, and the technique for producing the mixture lacks the kind of reliability demanded of an analysis of this type.

SUMMARY OF THE INVENTION

There has continued to remain, therefore, a need for an apparatus capable of accurately and consistently determining the blood group and Rhesus positive and negative factor of a blood sample that is not subject to the disadvantages of the devices of the prior art. It is a principal object of this invention to provide such an apparatus. It is a further object of this invention to provide an apparatus that is consistent in producing accurately analyzable blood sample-reactant mixtures. It is a still further object of this invention to provide an apparatus consistently accurate in its analysis of blood sample-reactant mixtures.

These various objects have been met in accordance with this invention by an apparatus comprising, in general, a housing or console containing the various components by means of which a blood sample analysis is made, including an analysis holder for holding the blood samples, reactants and mixtures thereof; distribution means in the form of needles and pumps for displacing blood samples and reactants to form analyzable mixtures; means for analyzing the agglutination reactions of the mixtures; and display means, both graphic and photographic, for displaying the results of the analyses of the mixtures. More particularly, the apparatus of this invention comprises an analysis holder containing a series of cavities designed to hold blood samples, a corresponding series of cavities to hold agglutination reactants, and a still further corresponding series of cavities designed to receive blood sample-reactant mixtures. Means are provided for displacing the analysis holder in conjunction with cooperative displacement of the distribution needle-pump means for moving blood samples and reactants from their respective cavities in the analysis holder into the blood sample-reactant mixture cavities where analysis of the agglutination reaction is effected.

DESCRIPTION OF THE DRAWINGS

In the drawings, which illustrate that which is presently regarded as the best mode of carrying out the invention.

DESCRIPTION OF THE PREFERRED EMBODIMENT

Figure 1A:
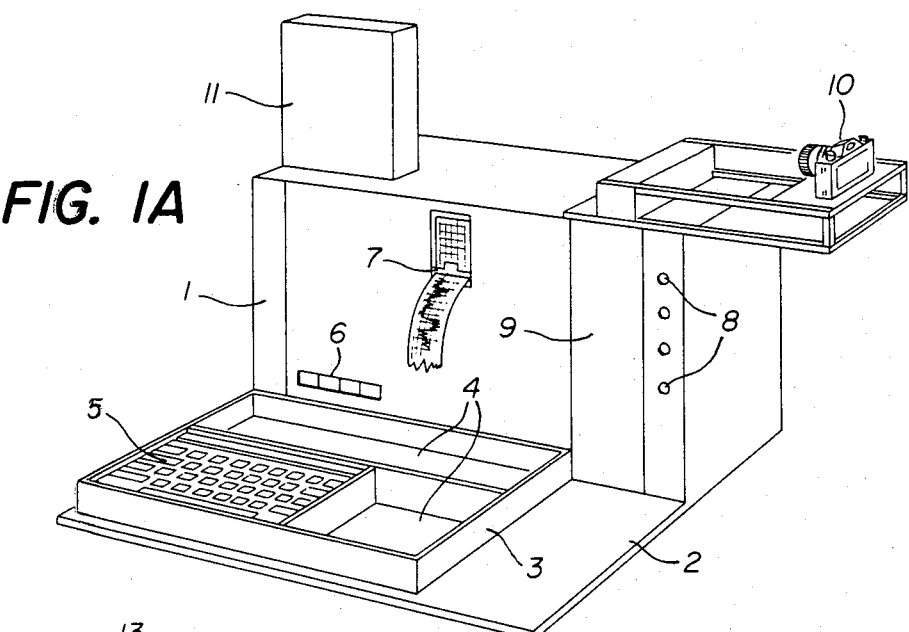
FIG. 1A is a perspective view of the blood group analyzing apparatus of this invention.
Figure 1B:
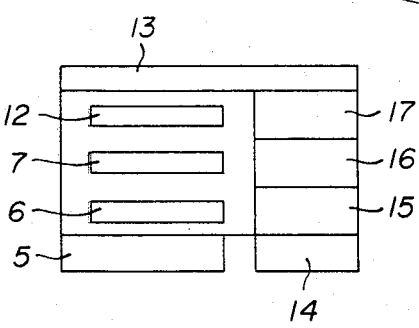
FIG. 1B is a schematic of the components comprising the apparatus of FIG. 1A.

Turning now to the drawings, an apparatus for determining the blood group of an individual in accordance with this invention is illustrated in FIG. 1, and comprises a housing or console 1 for housing the various components or means of the apparatus. Housing 1 is provided with a cover 2 adapted to fold down, as shown, when the apparatus is ready for use. Fitted to cover 2 is a frame 3 defining a plurality of storage trays 4 and a keyboard 5 by which the various functions of the apparatus are controlled. Arranged on the front surface of housing 1 are means 6 for displaying the functions controlled by keyboard 5, a printer 7 for graphically representing the results of the analysis performed by the apparatus, a series of signal lights 8 corresponding to the different apparatus functions and an opening 9 providing access to the blood analysis holders. Located on the top of housing 1 is a camera 10 and a screen for visual display of the results of analyses accommodated within a second, but smaller, housing 11, the side of which may be adapted as a chin rest for use by the patient while his photograph is being taken. Housing 1 contains the various components of the blood analyzing apparatus of this invention. As schematically illustrated in FIG. 1B. these components comprise, in addition to those various means already discussed with respect to FIG. 1A, a graphic recorder 12, a photographic assembly 13 comprising camera 10 and screen housing 11, assembly 14 for carrying blood analysis holders, a bank or block of distribution needles 15 for distributing blood and agglutination reactants, and a bank of pumps 17 designed to function in conjunction with distribution needles 15. These various components of the blood analysis apparatus of this invention are described in more detail hereinafter.

Figure 2:
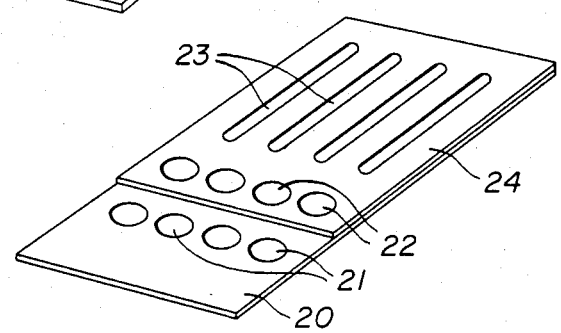
FIG. 2 is a perspective view of a preferred embodiment of the blood analysis holder of the apparatus of FIG. 1.

Referring now to FIG. 2, there is illustrated a blood analysis holder used in conjunction with the apparatus of FIG. 1 for determining an individual's blood group and Rhesus factor. The analysis holder comprises a sheet 20 of thermoplastic material, for example, provided with a first and second series of corresponding cavities 21 and 22 arranged in rows at right angles to the length of sheet 20. Cavities 21 are each designed to accommodate a specific quantity of a blood sample while cavities 22 are each designed to accommodate an antiserum used in the determination of blood groups A, B, AB or O, and the Rhesus positive or negative factor. Sheet 20 is further provided with blood sample-antiserum analysis cavities 23 in the form of channels which run longitudinally of sheet 20 and in extension of the centerlines passing through cavaties 21 and 22. Analysis cavities 23 serve as receptacles in which the blood sample is mixed with the antiserum, and in which the agglutination reaction is carried out.

Cavities 21, 22 and 23 are produced by deformation of sheet 20, the thermoplastic material of which is selected so as to be characteristically inert to the blood and antiserums used in the analysis. Sheet 20 is preferably transparent so that any coagulations produced by reaction of the blood samples and the antiserums in analysis cavities 23 can be observed directly through said sheet. A covering sheet 24 is preferably heat welded to sheet 20 in such manner as to seal off at least cavities 22 containing the antiserums, as well as analysis cavities 23 if desired.

Figure 3:
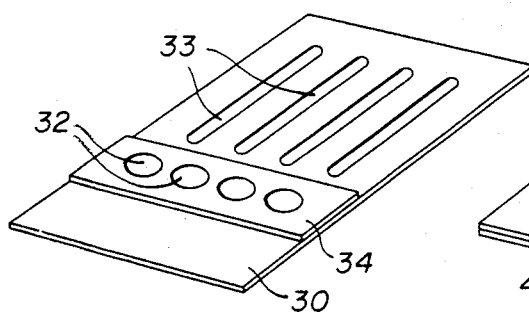
FIGS. 3 and 4 are perspective views of different embodiments of the blood analysis holder.

Another embodiment of the analysis holder is illustrated in FIG. 3 in which a sheet 30 of thermoplastic material is provided with cavities 32 designed to accommodate the antiserums used as reactants and, elongated cavities 33 designed to serve as reaction receptacles for the blood sample-antiserum mixtures. This embodiment differs from that of FIG. 2 in that it contains no cavities equivalent to cavities 21 for blood samples, and further in that the single row of antiserum cavities 32 is sealed off with a film 34 to the exclusion of analysis cavities 33. In this embodiment, blood samples are not incorporated separately into the analysis holder as in the embodiment of FIG. 2, but are introduced into analysis cavities 34 from another source by any suitable means such as the distribution and pump means described in detail hereinafter.

Figure 4:
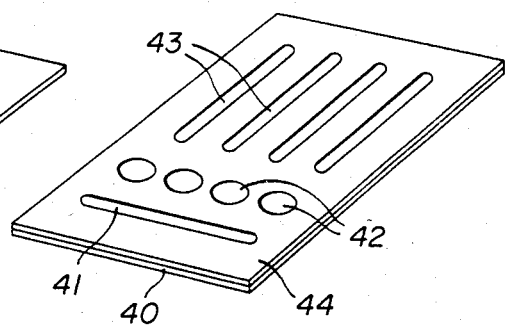

A still further embodiment of the analysis holder is shown in FIG. 4. In this embodiment, the analysis holder comprises a sheet 40 of thermoplastic material inert as to blood and antiserums as in the other embodiments, and provided with a blood sample cavity 41 in the form of an elongated channel running at right angles to the length of the sheet. Also provided is a series of cavities 42 similar to that of the other embodiments for receiving antiserums, and a series of analysis cavities in the form of elongated channels at right angles to blood sample cavity 41 and on centerlines with antiserum cavities 42, designed to receive the blood sample-antiserum mixes to be analyzed. A film 44 is used as a cover sheet to seal cavities 41, 42 and 43 and sheet 40.

Figure 5:
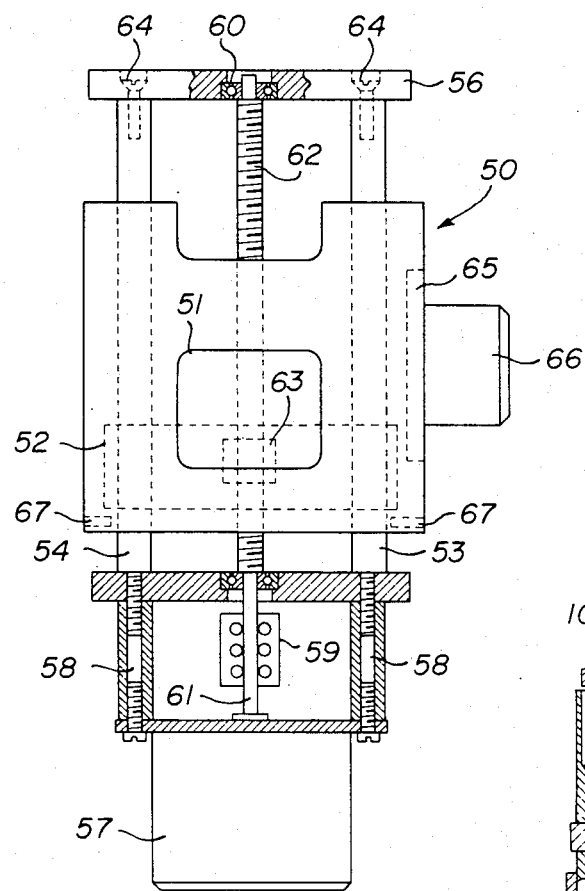
FIG. 5 is a plan view of the carrier plate of the apparatus of FIG. 1 designed to support the blood analysis holder.

Referring to FIG. 5, analysis holders 20 are arranged in the interior of the blood analysis apparatus of FIG. 1 on an analysis holder carrier plate 50 which is preferably made of metal. Carrier plate 50 is provided with a central aperture 51 which allows analysis by viewing the mixtures of blood samples and antiserums contained in the analysis holder. Carrier plate 50 is secured to a bracket 52 slidably mounted on horizontally disposed guide rods 53 and 54 which extend between mounting plates 55 and 56 and which are secured to the latter by bolts 64. Mounting plate 55 also supports drive motor 57 secured thereto as by bolts 58. Supported in bearings 59 and 60 in mounting plates 55 and 56, respectively, is drive shaft 61 of motor 57. Shaft 61 is provide with an endless screw 62 which is designed to engage gear 63 which is integrally formed as a part of bracket 52. Motion imparted to shaft 61 by means of motor 57 is thereby translated in to movement of carrier plate 50 along rods 53 and 54. In this manner, analysis holder 20 can be moved into different functional stations, i.e., successively under the distribution needles with respect to cavities 21, 22 and 23, and then with respect to the colorimetrical analysis means of the blood analyzing apparatus. A rotating cam 65 driven by motor 66 may be so mounted in the apparatus as to provide a rocking movement to carrier plated 50 about a horizontal axis, the purpose of this movement being to promote mixing of the blood sample-antiserum mixtures and and to facilitate the agglutination reaction. Analysis holder carrier plate 50 preferably has a cover, not shown, hinged thereto by pins 67. This cover is designed to be folded down onto plate 50, thus locking analysis holder 20 once it is in place.

Figure 6A:
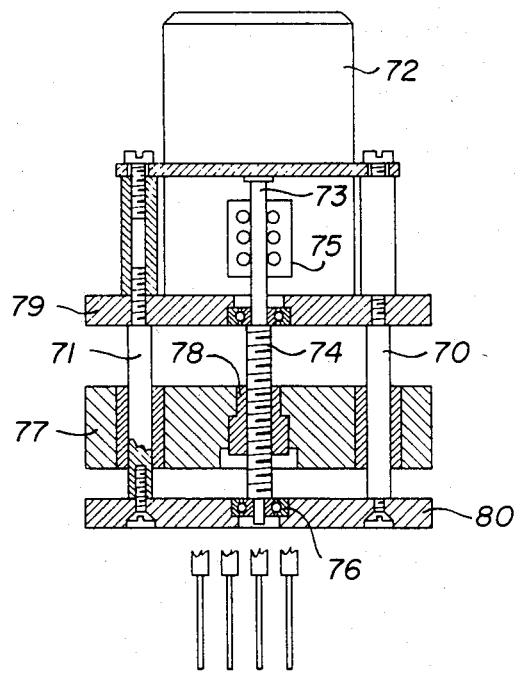
FIGS. 6A and 6B are, respectively, front and side elevation views of the needle distribution means of the apparatus of FIG. 1
Figure 6B:
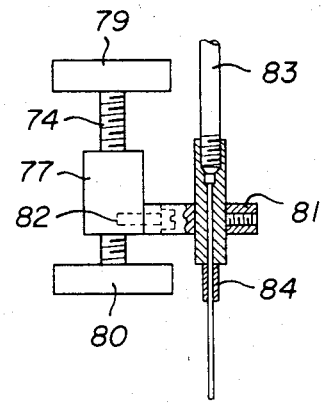

Illustrated in FIGS. 6A and 6B is a bank or block of distribution needles that serve to take blood samples from cavities 21 and antiserum reactants from cavities 22 of the analysis holder 20 of FIG. 2, to the blood sample-antiserum cavities 23 of the holder. The distribution needle block comprises two supporting rods 70 and 71 attached to end plates 79 and 80. Supported by rods 70 and 71 on end plate 79 is a motor 72 provided with a drive shaft 73 mounted for rotation in bearings 75 and 76 of end plates 79 and 80, respectively. Shaft 73 is provided with an endless screw 74 that engages the threaded orifice of block 78 upon which is mounted bracket 77 slidably supported on rods 70 and 71. Rotation of drive shaft 73, therefore, displaces bracket 77 between end plates 79 and 80. Associated with bracket 77 are a plurality of support arms 81 each secured to bracket 77 by fastening means 82. Each support arm 81 is adapted to receive a distribution needle 84 which is connected by a flexible conduit 83 at its top to a pumping means hereinafter described.

Figure 7:
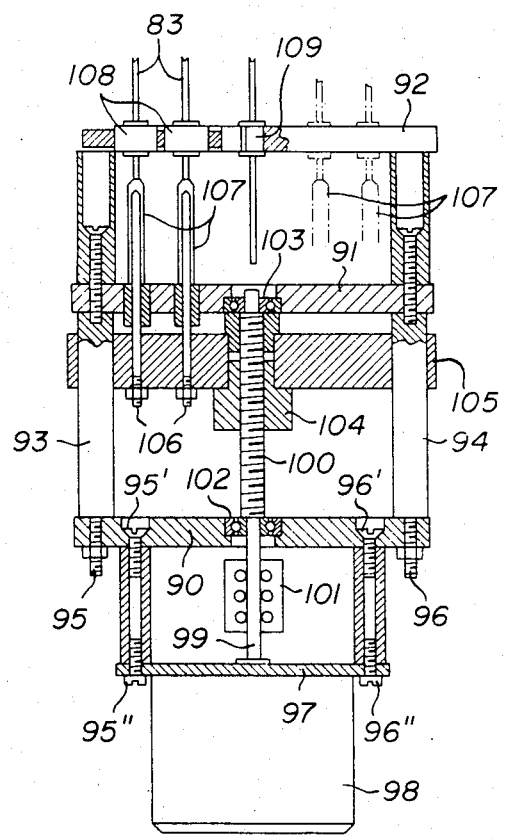
FIG. 7 is a side elevation of the pumping means of the apparatus of FIG. 1 shown in conjunction with the distribution needles of FIGS. 6A and 6B.

Turning now to FIG. 7, there is shown therein the pumping means to each unit of which one distribution needle 84 is connected by means of flexible conduit 83. The pumping means comprises three horizontally disposed plates 90, 91 and 92 supported by rods 93 and 94 to which they are secured by bolts 95 and 96. Secured to plate 90 by means of bolts 95'-95", 96'-96" is a support plate 97 on which is mounted motor 98. Output shaft 99 of motor 98 is mounted in bearings 101, 102, 103 and is provided with an endless gear 100 that engages a threaded orifice in block 104 on which is mounted bracket 105, the latter also being carried by rods 93 and 94.

Mounted in the pumping means of FIG. 7 are a plurality of pumps comprising a series of pistons 106 mounted in bracket 105 which cooperate with a corresponding series of cylindrical chambers 107 supported between plates 91 and 92. Three way electro magnetic valves 108 are secured to plate 92 and have upper outlets connected to one end of flexible conduits 83, the other ends of which are connected to distribution needles 84. The pump arrangement comprises four pistons 106 and four cylinders 107, together with four electro magnetic valves 108. These correspond to the four distribution needles 83, and the three series of cavities 21, 22 and 23 each comprising four cavities.

In operation, a pumping motion is provided pump means 106, 107 in synchronization with the also synchronized motions of carrier plate 50 and the block of distribution needles 84. By these synchronized motions, blood samples and antiserum reactants are withdrawn from cavities 21 and 22, respectively, of analysis holder 20 and deposited into cavities 23 for analysis of the resultant mixture by the analyzing means more specifically described in conjunction with FIG. 8. Pump means 106, 107 is provided with a central reciprocating valve 109 by means of which the entire system can be flushed with a diluent consisting, e.g., of demineralized water mixed with a detergent, whereby the entire circuit can be cleansed.

Figure 8:
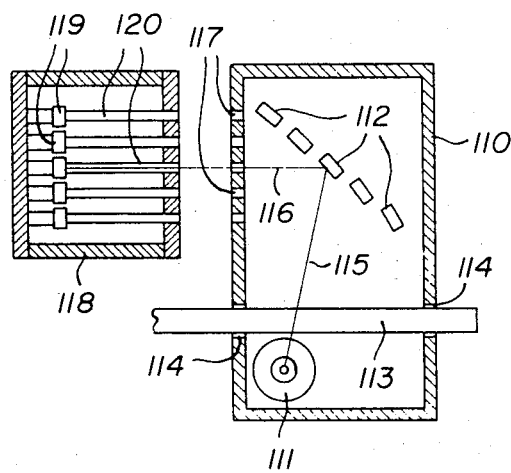
FIG. 8 is a diagrammatic representation of the means of the apparatus of FIG. 1 designed for analyzing the agglutination reaction of the mixtures in the analysis holder of FIG. 2.

FIG. 8 illustrates the analysis means of the apparatus of FIG. 1. It comprises a housing 110 containing a source of light, e.g., a filament lamp 111, and a series of flat mirrors 112, the number of which corresponds to the number of analysis cavities 23 in analysis holder 20. Carrier plate 113 traverses housing 110 through two slots 114 in opposite sides in such manner as to intersect the analyzing ray of light. This ray of light is reflected by one of mirrors 112. The resulting beam 116 passes through one of the apertures 117 arranged in one side of housing 110, and corresponding in number to the number of mirrors 112, and enters a second housing 118 provided with silicon detectors 119. The number of silicon detector cells corresponds to the number of apertures 117 and to the number of mirrors 112 which, as early stated, corresponds in turn to the number of analysis cavities 23. Aligned with each aperture 117 is a tubular member 120 located in housing 118 which acts as a guide for the corresponding reflected beam 116. The optical density measurement is carried out by transparency. If a reactant causes no agglutination of a blood sample in cavity 23, the silicon cell 119 generates no signal. On the other hand, if agglutination takes place, the ray 115 passes through the mixture contained in the corresponding cavitiy 23 in analysis holder 20 and generates a signal in silicon cell 119.

In order to improve the detection by silicon cell 119, a transparent plate 130 is mounted under blood analysis holder 20 in central aperture 51 of carrier plate 50. Transparent plate 130 has on the surface a series of fine parallel lines 131 forming a grid 132 extending perpendicular to the centerlines of longitudinal cavities 23 of analysis holder 20. If no agglutination takes palce in any one of the cavities 23, the corresponding light ray 115 will not be able to pass through the mixture in this cavity and the optical density analyzing means will not detect the grid 132. On the other hand, if agglutination takes place, the corresponding ray 115 will pass through the uncloudy portion of the mixture. Even if no agglutinated portion is located in the path of the light ray along cavity 23, e.g., if blood is agglutinated in the form of an elongated strip on one side of the cavity, several dark lines 131 will cut the light ray 115 and generate peaks on the graph. Such peaks indicate that an agglutinating reaction has been obtained.

Figure 9:
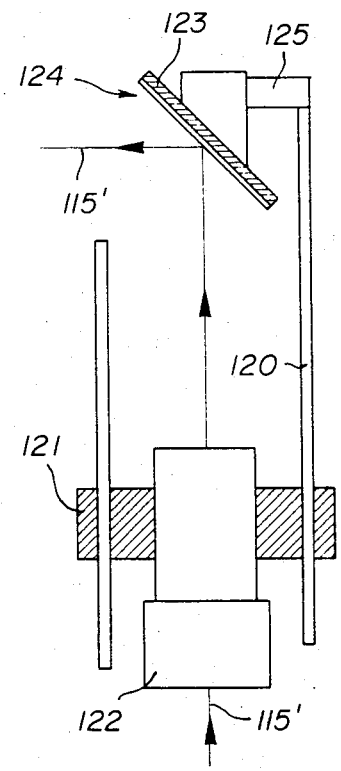
FIG. 9 is a diagrammatic representation of means designed for projecting an image of the blood sample-reactant mixture analysis onto a screen.
Figure 10:
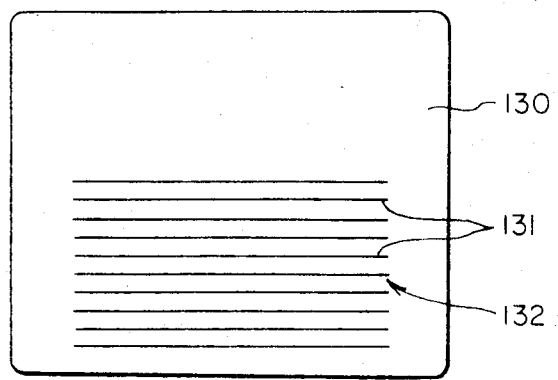
FIG. 10 is a representation of a transparent grid plate disposed below the blood analysis holder.

The episcope illustrated in FIG. 9 allows the image of the analysis holder 20 to be reflected, especially the area corresponding to the analysis cavities 23. The episcope consists of a support comprising two vertical rods 120 slidably supporting a member 121 which in turn carries a lens means 122. Positioning of the lens means in the path of light ray 115' permits focusing thereof onto reflective surface 123 of a flat mirror 124 secured by means 125 to one of the rods 120. Ray 115' reflected from mirror surface 123 can be projected onto a screen, e.g., frosted glass, mounted within photographic housing 11 of FIG. 1A. By this arrangement, it is possible to visualized analysis holder 20 directly, especially cavities 23. The episcope is arranged behind the colorimetrical means. Analysis holder 20 is placed above the optical density means and above the episcope which projects the image thereof onto the display screen of the photographic housing.

In operation of the apparatus of this invention, analysis holder 20 is placed in housing 1 on carrier plate 50 with sealed antiserum reactants in reactant cavities 22. Once analysis holder 20 is positioned in housing 1, blood samples are placed manually in blood sample cavities 21. The horizontal motion of carrier plate 50 and the vertical motions of the block of distribution needles 84 and pumping means 106, 107 being synchronized, blood samples and reactants are taken from cavities 21 and 22, respectively, by means of distribution needles 84 and deposited in analysis cavities 23, the opening and closing of conduits 83 being controlled by three way electro magnetic valves 108. Carrier plate 50 supporting analysis holder 20 with blood sample-reactant mixtures in cavities 23 is rocked gently by means of rotating cam 65 to enhance the mixing action and the agglutination reaction. Carrier plate 50 is then moved to the optical density analysis means where it is exposed to ray 115 and the detection of silicon cells 119. Graphic and photographic recordation of the results can be obtained as above described. The apparatus is flushed after each use cycle by means of reciprocating valve means 109 using a demineralized water-detergent mix. In order to facilitate the agglutination reactions especially the reaction to determine the Rhesus factor, the distribution needles 84 can be at least partially secured in heater sleeves designed to keep the mixtures of blood sample and reactant at a suitable temperature, i.e., about 37° C. To this end, the sleeves are equipped with small electrical resistances connected to a thermostatic device.

Reference in this disclosure to details of the specific embodiment is not intended to restrict the scope of the appended claims, which themselves recite those features regarded as essential to the invention.

I claim:

1. An apparatus for analyzing a blood sample which is mixed with an agglutinating reactant and subjected to optical density analysis, which comprises: a carrier plate provided with a centrally located aperture; means for horizontally mounting said carrier plate for lateral reciprocating movement and for rocking motion about a horizontal axis perpendicular to the axis of lateral movement; a transparent plate mounted in said centrally located aperture provided with a plurality of parallel lines forming a grid; a blood sample analysis holder mounted on the top surface of said carrier plate above said grid plate provided with a plurality of agglutinating reactant cavities and a corresponding number of elongated blood analysis cavities, the center line of each analysis cavity coinciding with a centerline of a corresponding reactant cavity and the centerlines of all of the analysis cavities being perpendicular to the lines of said grid plate; a distribution needle block mounted for vertical reciprocating movement in which are mounted a plurality of distribution needles corresponding in number to the number of analysis cavities in said analysis holder; a pump block mounted for reciprocating movement in which are mounted a plurality of reciprocating distribution pumps corresponding in number to the number of distribution needles in the distribution needle block, each pump being connected by means of a flexible conduit to a corresponding distribution needle; and an optical density analyzer associated with said carrier plate and said grid plate comprising a plurality of analyzing units corresponding in number to the number of analyzing cavities in said analysis holder; the various described movements being synchronized so that, in sequence, agglutinating reactant is drawn from each agglutinating reactant cavity by its corresponding distribution pump into its corresponding distribution needle, the agglutinating reactant in each distribution needle is discharged into its corresponding blood analysis cavity for reaction with a blood sample, a rocking motion is applied to said carrier plate to mix the agglutinating reactant and blood sample in each blood analysis cavity, and the resultant agglutinating reactant-blood mixture in each analysis cavity is analyzed by its corresponding optical density analyzing unit functioning in conjunction with said grid plate.

2. An apparatus according to claim 1 in which said carrier plate is also provided with a plurality of blood sample cavities, the number of which corresponds to the number of analysis cavities and the centerline of each of which coincides with the centerline of a corresponding analysis cavity, the various described movements being further synchronized so that a blood sample is withdrawn from each blood sample cavity by its corresponding distribution pump into its corresponding distribution needle for subsequent discharge into its corresponding blood analysis cavity.

* * * * *